United States Patent [19]
Nakamura et al.

[11] Patent Number: 5,743,847
[45] Date of Patent: Apr. 28, 1998

[54] STEREOSCOPIC ENDOSCOPE HAVING IMAGE TRANSMITTING OPTICAL-SYSTEM AND PUPIL DIVIDING UNIT THAT ARE AXIALLY MOVABLE WITH RESPECT TO EACH OTHER

[75] Inventors: Motokazu Nakamura; Tetsumaru Kubota, both of Hachioji, Japan

[73] Assignee: Olympus Optical Co., Ltd., Tokyo, Japan

[21] Appl. No.: 577,239

[22] Filed: Dec. 22, 1995

[30] Foreign Application Priority Data

Jan. 13, 1995 [JP] Japan ............... 7-004312

[51] Int. Cl.$^6$ ............................................. A61B 1/06
[52] U.S. Cl. ............................... 600/166; 600/111
[58] Field of Search ......................... 600/111, 166; 348/45; 359/477

[56] References Cited

U.S. PATENT DOCUMENTS

| | | | |
|---|---|---|---|
| 4,061,135 | 12/1977 | Widrian et al. | 600/166 |
| 4,364,629 | 12/1982 | Lang et al. | 600/166 |
| 4,779,613 | 10/1988 | Hashiguchi et al. | 600/169 |
| 5,222,477 | 6/1993 | Lia | 600/166 |
| 5,295,477 | 3/1994 | Janfaza | 600/166 |
| 5,588,948 | 12/1996 | Takahashi et al. | 600/111 |

FOREIGN PATENT DOCUMENTS

| | | | |
|---|---|---|---|
| 289924 | 5/1991 | Germany | 600/166 |
| 43 41 975 A1 | 7/1994 | Germany. | |
| 57-69839 | 4/1982 | Japan. | |
| 6-59199 | 3/1994 | Japan. | |

*Primary Examiner*—John P. Leubecker
*Attorney, Agent, or Firm*—Frishauf, Holtz, Goodman, Langer & Chick

[57] ABSTRACT

A pupil division type stereoscopic endoscope includes a relay lens system, a pupil dividing stop unit, and a camera head. The relay lens system includes by an image-forming lens for forming an image of an object, and a relay lens portion for transmitting the image formed by the image-forming lens, and has one optical axis. The pupil dividing stop unit divides an object image transmitted by the relay lens system to obtain a plurality of object images which are to be subjected to stereoscopic observation. The camera head receives the plurality of object images that are formed through division by the pupil dividing stop unit and performs stereoscopic observation. The relay lens system and the pupil dividing stop unit constitute an integral optical, system yet are axially movable relative to one another. The main body of the optical lens system side and the camera head can be attached with and detached from each other.

8 Claims, 7 Drawing Sheets

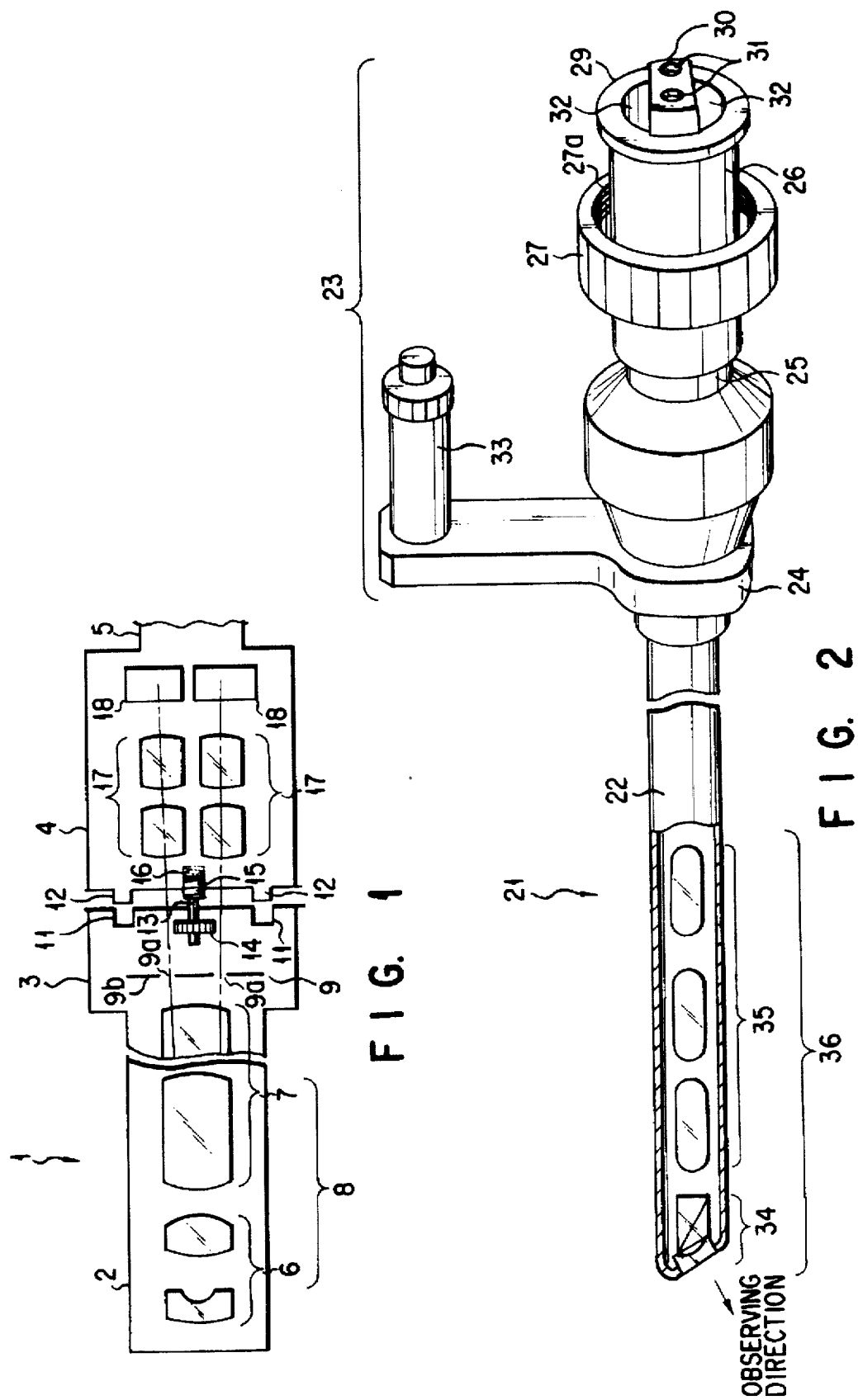

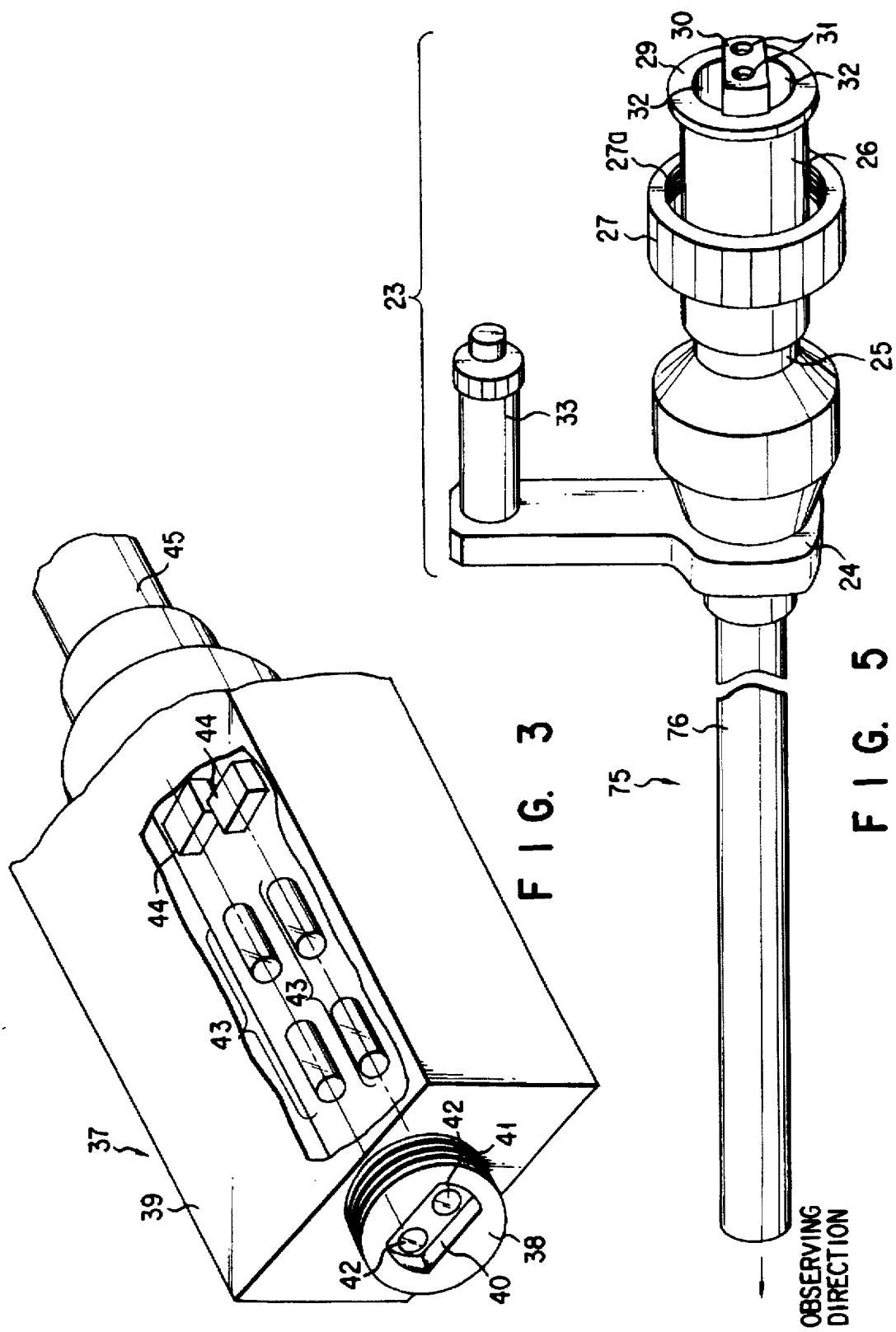

STEREOSCOPIC ENDOSCOPE HAVING IMAGE TRANSMITTING OPTICAL-SYSTEM AND PUPIL DIVIDING UNIT THAT ARE AXIALLY MOVABLE WITH RESPECT TO EACH OTHER

BACKGROUND OF THE INVENTION

1. Field of the Invention

The present invention relates to a pupil division type stereoscopic endoscope for stereoscopically observing an object by utilizing a relay lens system having one optical axis.

2. Description of the Related Art

A medical endoscope is known which observes organs in the body cavity by inserting its elongated inserting portion into the body cavity. An industrial endoscope is also known which observes flaws or damage in the internal components, e.g., pipes, of a boiler gas turbine plant. Most of the conventional endoscopes observe the internal state of an observation target as a flat surface without a sense of perspective. With such endoscopes, it is difficult to observe fine corrugations on the surface of, e.g., the inner wall of the body cavity. In order to cope with this problem, recently, a stereoscopic endoscope which observes an object stereoscopically is proposed (see Jpn. Pat. Appln. KOKAI Publication No. 57-69839).

According to a stereoscopic endoscope of this type, generally, right and left object images obtained by two objective lenses having a parallax therebetween are transmitted through separate image guides and relay lenses, and the respective object images are separately sensed by solid-state imaging elements, e.g., charge-coupled devices (CCDs), thereby obtaining right and left observation images.

Recently, a so-called pupil division type stereoscopic endoscope is proposed in which an optical image obtained by one optical system is divided into right and left object images by a pupil dividing means, and the two object images are sensed separately (Jpn. Pat. Appln. KOKAI No. 6-59199). In this pupil division type stereoscopic endoscope, the number of lenses to be employed can be decreased, so that the endoscope can be fabricated compact at a low cost.

The pupil dividing type stereoscopic endoscope has a hard inserting portion incorporating one objective lens and an image transmitting means comprising one relay lens for transmitting an image formed by the objective lens. In addition to the inserting portion, this stereoscopic endoscope has a large-diameter operational holding portion. The operational holding portion incorporates a pupil dividing means for dividing an object image transmitted through the image transmitting means, thereby obtaining right and left images, and an imaging means for focusing and forming the right and left object images that are divided by the pupil dividing means. In this stereoscopic endoscope, a television camera and the operational holding portion incorporating the pupil dividing means are integrated, and the inserting means and the operational holding means incorporating the pupil dividing means are detachably arranged.

Generally, since an endoscope must observe the interior of the body cavity with less invasion to the body, its inserting portion is particularly required to have a small diameter. At the same time, however, in the stereoscopic endoscope as described above, a sufficiently large parallax is required in performing high-quality stereoscopic observation, and the right and left object images must have a sufficiently high brightness.

When the stereoscopic endoscope disclosed in Jpn. Pat. Appln. KOKAI No. 6-59199 is formed to have a sufficiently large parallax and to provide a sufficiently high brightness in the right and left object images, it will have a structure as follows due to the decrease in diameter of the inserting portion.

To decrease the diameter of the inserting portion, the diameter of the image-forming lens and the diameter of the image transmitting means must be decreased. Then, the light beam emerging from the transmitted object image is decreased.

To obtain a sufficiently large parallax, the light beam must be divided by a pupil dividing means whose two pupil apertures are separate from the optical axis as far as possible.

When the decrease in diameter of the inserting portion and the sufficiently large parallax are to be obtained in this manner, the pupil dividing means must be formed by setting the two pupil apertures as close as possible to the two end regions of a thin light beam transmitted through a relay lens system, as shown in FIG. 13.

In the conventional stereoscopic endoscope, a mounting portion is provided between the inserting portion and the operational holding portion to attach and detach them to and from each other. This mounting portion requires a predetermined gap in the radial direction from the inserting portion and the operational holding portion, so that it can perform mounting easily. Upon mounting, the inserting portion and the operational holding portion are sometimes offset in the radial direction due to this gap. When the inserting portion and the operational holding portion are offset, the light beam in the inserting portion and the pupil dividing means integrated with the operational holding means are offset each other in the radial direction. If regions for the pupil apertures are arranged to correspond to the two marginal ends of the light beam, the light beam cannot be received sufficiently by either one of the two separated apertures, as shown in FIG. 14. As a result, the image after the aperture that cannot receive the light beam sufficiently becomes dark and the brightness of the image becomes insufficient or non-uniform, so that high-quality stereoscopic observation cannot be performed.

In this manner, to ensure the brightness of the right and left images while decreasing the diameter of the inserting portion and providing a sufficiently large parallax, a closely related coupling structure in which a radial offset does not occur between the light beam transmitting portion and the pupil dividing means must be employed. However, in order to facilitate mounting of the operational holding portion and the inserting portion, a certain offset is inevitably present between the inserting portion and the pupil dividing portion. In this conventional stereoscopic endoscope, as the regions for the pupil apertures cannot be arranged to correspond to the two marginal ends of the light beam, a decrease in diameter of the inserting portion is particularly limited.

SUMMARY OF THE INVENTION

The present invention has been made in view of the above problem, and has as its object to provide a pupil division type stereoscopic endoscope in which an observation means can be attached to and detached from an image transmitting portion in an inserting portion as well as a sufficiently large parallax and a sufficiently high brightness in a plurality of object images can be maintained despite that a decrease in diameter of the inserting portion can be achieved.

The above object can be achieved by a pupil division type stereoscopic endoscope comprising:

image transmitting optical system having an image-forming lens for forming an image of an object to transmit the image formed by the image-forming lens, the image transmitting optical system having an optical axis;

a pupil dividing unit for dividing an object image transmitted by the image transmitting optical system into a plurality of object images having a parallax therebetween;

an observation unit for receiving the plurality of object images obtained through division by the pupil dividing unit, thus performing stereoscopic observation;

a main body incorporating the image transmitting optical system and the pupil dividing unit therein; and a connecting unit for coupling the main body and the observation unit to each other, the connecting unit detachably arranging the main body and the observation unit.

With this stereoscopic endoscope, divided object images after the pupil dividing means can be entirely received by the imaging means without a loss. With this arrangement, the following structure can be employed easily.

(1) Since attachment and detachment are not performed in the unit body from the image transmitting optical means to the pupil dividing unit, each component in this portion can have a great tolerance, and a radial offset in the portion from the image transmitting optical system in the inserting portion to the pupil dividing unit can be minimized.

(2) The imaging means in the camera head which does not invade the living body is set to have a sufficiently large size within a range not interfering with the operability of the operator, and the imaging means is detachably arranged between the pupil dividing unit and the camera head. Thus, even if the imaging means is mounted with an offset between the unit and the camera head and the pupil dividing unit of the unit and the imaging means in the camera head are slightly displaced from each other in the radial direction, due to the margin of the imaging means, the object images after the pupil dividing unit can be entirely received by the imaging means and the like.

As described above, the radial offset between the image transmitting optical system and the pupil dividing unit is minimized with the structure (1). Due to the structure (2), even if the offset occurs more or less during mounting, the divided images after the pupil dividing unit can be entirely received by the imaging means. Thus, even if the object image is divided by the pupil dividing unit in which a plurality of pupil apertures are separated as far as possible by effectively utilizing the regions corresponding to the two marginal end regions of a thin light beam, the brightness of each image can always be maintained.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 1 is a diagram for schematically explaining the arrangement of a rigid stereoscopic endoscope according to the first embodiment of the present invention;

FIG. 2 is a perspective view of a rigid stereoscopic endoscope according to the second embodiment of the present invention;

FIG. 3 is a partially cutaway perspective view of the rigid stereoscopic endoscope according to the second embodiment;

FIG. 5 is a perspective view of a rigid stereoscopic endoscope according to the third embodiment of the present invention;

Figure 4:
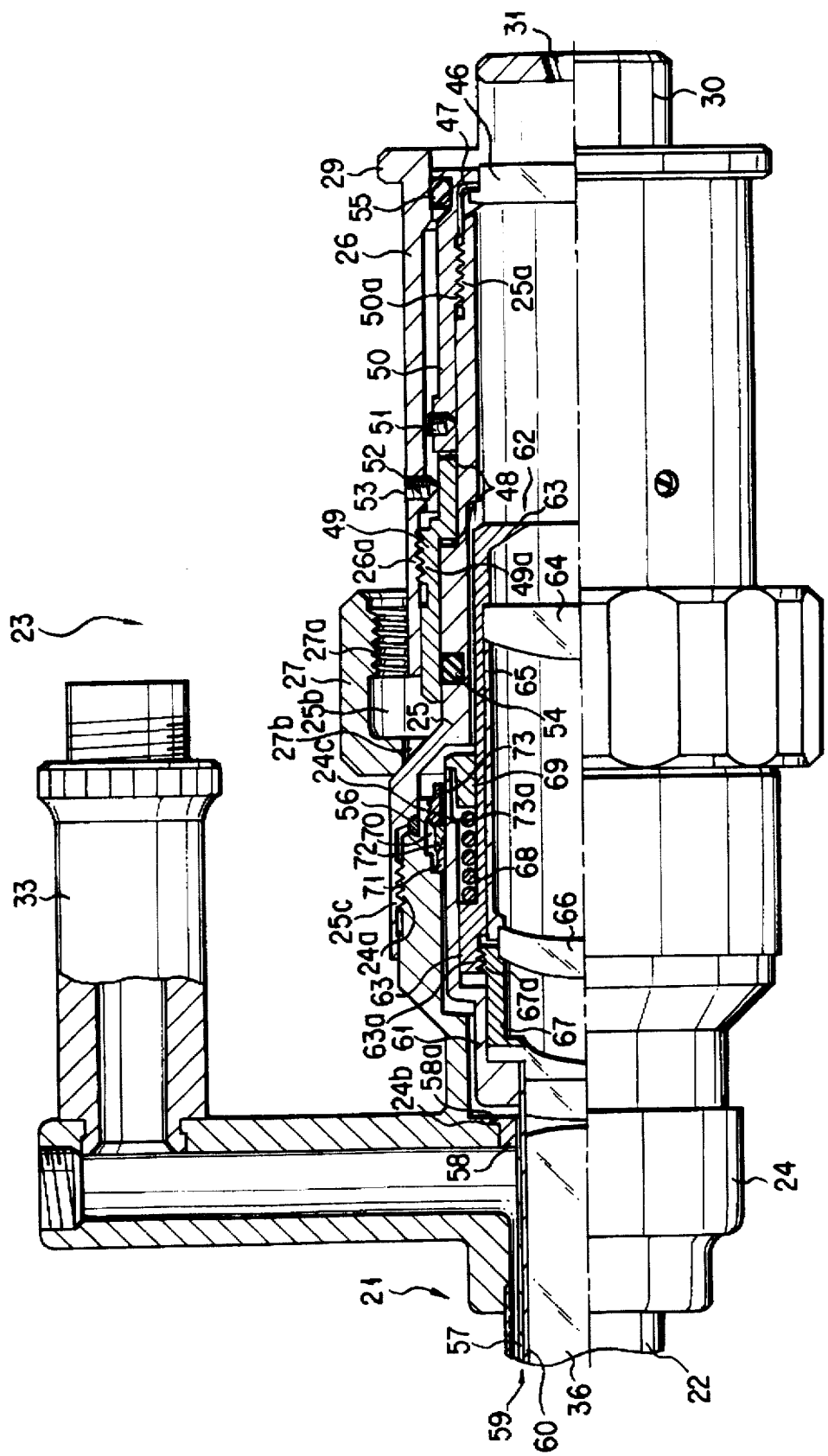
FIG. 4 is a sectional view showing the operational holding portion of the rigid stereoscopic endoscope according to the second embodiment.

DETAILED DESCRIPTION OF THE PREFERRED EMBODIMENTS (First Embodiment)

FIG. 1 is a diagram for schematically explaining the arrangement of a stereoscopic endoscope 1 that stereoscopically observes an object. The stereoscopic endoscope 1 has a rigid inserting portion 2, a large-diameter operational holding portion 3 coupled to the inserting portion 2, and a camera head 4 detachable from the operational holding portion 3. The camera head 4 has a signal cable 5 extending backward.

The hard inserting portion 2 incorporates an objective lens 6 consisting of a plurality of lenses, and a relay lens portion 7 consisting of an array of a plurality of lenses from its distal end side. The objective lens 6 is an image-forming lens for forming the image of an object observed through it. The image formed by the objective lens 6 is transmitted by the relay lens portion 7 serving as an image transmitting means and guided to a pupil dividing means (to be described later). The objective lens 6 and the relay lens portion 7 constitute one relay lens system 8.

A pupil dividing stop 9 serving as the pupil dividing means is provided to the operational holding portion 3 of the rigid stereoscopic endoscope 1. Although the pupil dividing field stop 9 is used as the divided pupil unit, for example, a pupil dividing prism or a deflecting plate may be employed instead.

The pupil dividing stop 9 is made of a plate member 9b which has two pupil apertures 9a. The apertures 9a are arranged symmetric with respect to the axis of the relay lens system 8. They are spaced by a distance long enough to maintain an adequate parallax. This pupil dividing stop 9 divides, with its two pupil apertures 9a, the object image into two portions corresponding to the two marginal ends of the effective light beam of the object image. When the relay lens system 8 or the pupil dividing stop 9 is indexed in the radial direction, a sufficient amount of light beams pass through the two pupil apertures 9a, thereby maintaining the brightness of the right and left images.

The operational holding portion 3 incorporating the pupil dividing stop 9 is integrally coupled to the inserting portion 2. The inserting portion 2 and the operational holding portion 3 constitute an optical lens system main body into which an optical system having the image transmitting optical system (image transmitting means) and the pupil dividing unit (pupil dividing means) are integrally incorporated. The relay lens system 8 and the pupil dividing stop 9 constitute an integral optical system, and this integral optical system is integrally incorporated in the main body.

The inserting portion 2 and the operational holding portion 3 form an airtight structure that does not allow communication of a gas between its inner and outer portions. The image transmitting means and the pupil dividing means are provided in this airtight structure.

A plurality of positioning holes 11 are formed in the rear end face of the operational holding portion 3, and positioning pins 12 to fit in the positioning holes 11 project from the camera head 4. A connecting screw 13 is rotatably mounted on the rear end portion of the operational holding portion 3. The connecting screw 13 is rotated by a knob 14, and is supported such that it will not be removed from the operational holding portion 3 although it is allowed to move by a predetermined amount with respect to the operational holding portion 3 in the axial direction. A male screw portion 15 is formed on the connecting screw 13, and the male screw portion 15 is screwed into a screw hole 16 formed in the camera head 4 to correspond to it. The positioning pins 12 are fitted in the positioning holes 11 and the male screw portion 15 of the connecting screw 13 is screwed into the screw hole 16 of the camera head 4, thereby constituting a connecting means that mounts the camera head 4 on the operational holding portion 3. This connecting means detachably arranges the operational holding portion 3 and the camera head 4.

In this connecting structure, when the positioning holes 11 and the positioning pins 12 are fitted to each other, a predetermined gap is maintained between them in the radial direction, so that the camera head 4 can be mounted to the operational holding portion 3 easily. After the positioning holes 11 and the positioning pins 12 are fitted to each other, the male screw portion 15 of the connecting screw 13 is screwed into the screw hole 16 of the camera head 4, so that the operational holding portion 3 and the camera head 4 are positioned and coupled to each other while the amount of radial offset between the operational holding portion 3 and the camera head 4 is suppressed within this gap.

The camera head 4 is provided with imaging means for forming and imaging the right and left object images divided by the pupil dividing stop 9 serving as the pupil dividing means. Each imaging means is constituted by an imaging lens 17 consisting of a plurality of lenses and solid-state imaging elements, e.g., charge-coupled devices (CCDs). Each CCD 18 is electrically connected to a control unit (to be described later) through the signal cable 5.

The stereoscopic observing/imaging system of the rigid stereoscopic endoscope 1 has been described so far. Although not shown, the endoscope 1 also incorporates a general illumination optical system. The illumination optical system supplies illumination light from a light source unit (not shown) to the object through a light guide cable (not shown).

The control unit (not shown) is electrically connected to the camera head 4 through the signal cable 5. The control unit drives the CCDs 18, processes electrical signals output from the CCDs 18, and displays right and left object images on a monitor (not shown) alternately, e.g., 30 times per second. The observer can observe the object images displayed on the monitor as a stereoscopic image through light-shielding glasses. The light-shielding glasses shield right and left eyes alternately in synchronism with images displayed on the monitor. This gives the sense of the stereoscopic effect to the observer by utilizing after image. The observer can observe the images as a stereoscopic image due to the parallax between the right and left object images incident on the pupil of the objective lens 6.

Referring to FIG. 1, the portion of the rigid stereoscopic endoscope 1 from its relay lens system 8 to pupil dividing stop 9 is integrally formed, and indexing of the relay lens system 8 and pupil dividing stop 9 in the radial direction is ensured. Hence, any offset does not occur between the object image transmitted by the relay lens system 8 and the pupil apertures 9a of the pupil dividing stop 9, so that the object image can be divided into right and left object images having a sufficiently high brightness and a sufficiently large parallax therebetween.

To connect the rigid stereoscopic endoscope 1 and the camera head 4 to each other, the positioning pins 12 provided to the camera head 4 are fitted in the positioning holes 11 formed in the operational holding portion 3, the operational holding portion 3 and the camera head 4 are placed to abut against each other, and the male screw portion 15 of the connecting screw 13 is screwed into the screw hole 16 of the camera head 4. Since a gap is present between the positioning holes 11 and the positioning pins 12 in the radial direction, the rigid stereoscopic endoscope 1 and the camera head 4 are coupled to each other such that they can be offset from each other in the radial direction within the range of the gap.

In this manner, the rigid stereoscopic endoscope 1 and the camera head 4 can be offset from each other in the radial direction, and upon coupling of the rigid stereoscopic endoscope 1 and the camera head 4, the pupil dividing stop 9 provided to the operational holding portion 3 and the imaging lenses 17 and CCDs 18 provided to the camera head 4 are slightly relatively offset from each other in the radial direction. However, since the imaging lenses 17 and the CCDs 18 are formed to have a sufficiently large size to allow this offset, the right and left object images passing through the pupil apertures 9a of the relay lens system 8 can be entirely received by the CCDs 18.

As the image transmitting means and the pupil dividing means are not detachable from each other, a radial offset between them can be decreased. As a result, the aperture regions of the pupil dividing means can be located to correspond to the marginal end portions of the light beam the spot diameter of which is decreased upon decrease in diameter of the inserting portion 2 of the rigid stereoscopic endoscope 1, and the brightness of the right and left images after division can always be obtained without a loss. Even if the rigid stereoscopic endoscope 1 and the camera head 4 are coupled to each other with a radial offset between them, the influence of this offset is small, and the light beams from the right and left object images are entirely received by the corresponding CCDs 18. Thus, the brightness of the right and left images is always maintained.

(Second Embodiment)

A rigid stereoscopic endoscope and a camera head according to the second embodiment of the present invention will be described with reference to FIGS. 2 to 4.

FIG. 2 is a perspective view of a rigid stereoscopic endoscope 21 according to the second embodiment. The operational holding portion and the pupil dividing means of the rigid stereoscopic endoscope 21 are rotatable relative to each other. The rigid stereoscopic endoscope 21 has a hard small-diameter inserting portion 22 and an operational holding portion 23 coupled to the inserting portion 22. The operational holding portion 23 is constituted by a main body 24 coupled to the inserting portion 22, an outer cylinder support portion 25 coupled to the main body 24, an outer cylinder 26 with a stop, and a connecting ring 27. The outer cylinder 26 is integrally supported on the outer surface of the outer cylinder support portion 25 to be stationary in the axial direction but rotatable about the axis. The connecting ring 27 is supported on the outer surface of the outer cylinder 26 to be movable in the axial direction and rotatable about the axis.

A female screw 27a for mounting a camera head (to be described later) is formed on the inner surface of the connecting ring 27. In FIG. 2, a flange portion 29 having a function of preventing removal of the connecting ring 27 is provided to the outer surface of the right side of the outer cylinder 26. A camera head mounting portion 30 is provided to the right-side end portion of the outer cylinder 26 in FIG. 2. When attaching and detaching a camera head 37 (to be described later), the camera head mounting portion 30 is inserted in the camera head 37. The camera head mounting portion 30 is a projection having an oblate cross section. The portion 30 has two countersinks 31 and two holes 32. The countersinks 31 are located symmetric with respect to the axis of the support portion 25 of the outer cylinder 26. They serve as a pupil dividing stop (later described). The holes 32 are made in the opposing sides of the camera head mounting portion 30 and used to wipe the cover glass of the endoscope. The main body 24 is provided with a light guide cable mounting portion 33 serving as an illumination light receiving portion. The light guide cable mounting portion 33 is coupled to an illumination optical system (not shown) provided in the rigid stereoscopic endoscope 21.

The inserting portion 22 incorporates an objective lens 34 consisting of a plurality of lenses including a prism for oblique-vision observation, and a relay lens portion 35 consisting of a plurality of lens groups from its distal end side. The objective lens 34 and the relay lens portion 35 constitute one relay lens system 36, thus constituting an image-forming means for forming the image of an object and an image transmitting means for transmitting the image formed by the image-forming means. The image of the object transmitted by the image transmitting means is divided by the two countersinks 31 serving as the pupil dividing stop. The two countersinks 31 serving as the pupil dividing stop comprise tapered holes each having a narrow distal-end incident side and a wide proximal-end exit side. The centers of the countersinks 31 are arranged to be symmetric about the optical axis of the relay lens system 36. The countersinks 31 constitute a pupil dividing means for dividing the right and left object images incident on the right and left pupil portions of the relay lens system 36. A portion from the relay lens system 36 to the countersinks 31 of the pupil dividing means is incorporated as a unit in the main body portion of the rigid stereoscopic endoscope 21 in which the inserting portion 22 and the operational holding portion 23 are integrally formed, thus constituting an integral optical lens body.

FIG. 3 shows the camera head 37. The camera head 37 has an endoscope mounting portion 38 for mounting the camera head mounting portion 30 of the rigid stereoscopic endoscope 21 thereon, a camera head holding portion 39 coupled to the endoscope mounting portion 38, and a cable 45 to be connected to a control unit (not shown).

An elongated recessed portion 40 in which the elongated projecting portion of the camera head mounting portion 30 is to be fitted, and a male screw 41 to be connected to the female screw 27a of the connecting ring 27 are formed on the endoscope mounting portion 38.

When the elongated projecting portion of the camera head mounting portion 30 and the elongated recessed portion 40 of the endoscope mounting portion 38 are fitted to each other, a predetermined gap is maintained between them in the radial direction, so that the camera head mounting portion 30 and the endoscope mounting portion 38 can be mounted with each other easily. After the elongated projecting portion of the camera head mounting portion 30 and the elongated recessed portion 40 are fitted to each other, the connecting ring 27 of the rigid stereoscopic endoscope 21 is clamped, so that the camera head mounting portion 30 and the endoscope mounting portion 38 are positioned and coupled to each other while suppressing the amount of radial offset between them within the gap.

Right and left camera head cover glass plates 42 are provided in the elongated recessed portion 40. The camera head cover glass plates 42 pass the right and left object images sent from the rigid stereoscopic endoscope 21 therethrough and prevent water or the like from entering in the camera head holding portion 39.

The camera head holding portion 39 is provided with a pair of right and left optical imaging systems serving as a stereoscopic imaging means. Each optical imaging system is provided with an imaging lens 43 consisting of a plurality of lenses and an imaging element (CCD) 44 of the imaging means. Each of the pair of right and left optical imaging systems has a sufficiently large size for receiving all the light beams passing through the corresponding countersink 31 regardless of the offset during mounting, in the same manner as in the first embodiment described above. The right and left object images sent from the rigid stereoscopic endoscope 21 are transmitted to the imaging elements 44 to be converted into electrical signals. The electrical signals are then output to the control unit similar to that described in the above first embodiment.

The structure of the operational holding portion 23 of the rigid stereoscopic endoscope 21 will be described in detail with reference to FIG. 4. An endoscope cover glass plate 46 and a retaining ring 47 are fixed to the outer cylinder support portion 25 of the operational holding portion 23 by adhesion.

in order to form a vapor-free or hermetic structure that prevents vapor from entering from the outside to the optical system. A washer 48 for increasing slidability, a removal preventing ring 49, and another washer 48 are sequentially placed in the outer cylinder support portion 25 from the right side in FIG. 4, and a female screw 50a of a torque ring 50 is finally screwed onto a male screw 25a of the outer cylinder support portion 25. The rotation torque of the removal preventing ring 49 with respect to the outer cylinder support portion 25 is adjusted by adjusting the screwing amount of the torque ring 50 into the outer cylinder support portion 25, and thereafter the outer cylinder support portion 25 is positioned with three screws 51. The torque ring 50 apparently covers the adhering portion of the vapor-free structure of the outer cylinder support portion 25. Thereafter, the connecting ring 27 having a female screw 27a and a small-diameter removal preventing portion 27b is placed in the outer cylinder support portion 25 from the right side, and a female screw 26a of the outer cylinder 26 is screwed onto the male screw 49a of the removal preventing ring 49, thereby coupling the connecting ring 27 and the outer cylinder support portion 25 to each other. The outer cylinder 26 is provided with the flange portion 29 having a larger diameter than that of the removal preventing portion 27b. The flange portion 29 serves as a butting surface when mounting the camera head 37. A portion of the outer cylinder 26 which is to be screwed onto the removal preventing ring 49 can change the positions of the relay lens system 36 in the outer cylinder support portion 25 and the flange portion 29 serving as the butting surface relative to each other in the axial direction, and forms a focus adjusting structure of the rigid stereoscopic endoscope 21 with respect to the camera head 37. With this structure, focus adjustment can be performed in the last stage of the assembly of the endoscope. After focus adjustment, positioning is performed with a screw 52, and the screw 52 is covered with a rubber-based (e.g., a silicone rubber-based) adhesive 53 so that water will not enter from the screw hole. This arrangement forms a position adjusting means.

With the above arrangement, the outer cylinder support portion 25 and the torque ring 50 are fixed, and the removal preventing ring 49 and the outer cylinder 26 are fixed. The removal preventing ring 49 is sandwiched between the outer cylinder support portion 25 and the torque ring 50, so that it will not pivot with respect to or be removed from the outer cylinder support portion 25. Hence, the outer cylinder 26 coupled to the removal preventing ring 49 does not also pivot with respect to or is not removed from the outer cylinder support portion 25.

A watertight O-ring 54 is provided between the outer cylinder support portion 25 and the removal preventing ring 49, and a watertight O-ring 55 is provided between the torque ring 50 and the outer cylinder 26. A portion of the outer cylinder support portion 25 which is not covered with the removal preventing ring 49 or outer cylinder 26 forms a small-diameter relief portion 25b. When the connecting ring 27 is moved to the relief portion 25b and moved in the radial direction, the inner circumferential surface of the connecting ring 27 can be cleaned easily.

The outer cylinder support portion 25 is screwed and fixed on a male screw 24a of the main body 24 with its female screw 25c. At this time, a metal ring 56 having a trapezoidal section is sandwiched and squeezed by the female screw 25c and the male screw 24a, thus forming a vapor-free or hermetic structure that does not allow permeation of vapor.

An inner tube 57 covering a lens tube incorporating the relay lens system 36 (to be described later) is welded with a laser to an inner tube receptacle 58 in a vapor-free manner. A thin flange portion 58a of the inner tube receptacle 58 is placed in a groove 24b of the main body 24, and a laser beam is irradiated to the flange portion 58a in the axial direction to melt the tight-contact surface, thereby performing vapor-free laser welding which is more reliable than conventional laser welding in which a gap in the radial direction is buried. Although not shown, a cover glass plate having a side surface mounted with a metal film is soldered and fixed to the distal end side (left side in FIG. 4) of the inner tube 57, thus constituting a distal end vapor-free or hermetic structure.

As described above, adhesion of the retaining ring 47, squeezing of the metal ring 56, laser welding of the portion around the inner tube 57, and soldering of the distal end side cover glass plate prevent vapor from entering the inner optical system.

A lens tube unit 59 (to be described later) is inserted in the inner tube 57. The lens tube unit 59 consists of a lens tube 60 having a relay lens system 36 therein, a lens unit receptacle 61 coupled to the lens tube 60 with a solder or the like, and a lens unit 62 (to be described later).

The lens unit 62 has a structure as follows. A lens 64, a spacer tube 65, and a lens 66 are placed in a mask cylinder 63 from the left side in FIG. 4, and a male screw 67a of a lens retainer 67 is screwed into a female screw 63a of a mask cylinder 63, thus constituting the lens unit 62.

The lens unit 62 is placed in the lens unit receptacle 61, a spring 68 is placed in the lens unit receptacle 61, and the lens unit receptacle 61 is covered with a spring retainer 69. Thus, the lens unit 62 elastically pushes the axially non-fixed relay lens system 36 in the lens tube 60 with the spring 68, thereby preventing the relay lens system 36 from being removed to the right side in FIG. 4. Although not shown, the left side of the relay lens system 36 in FIG. 4 is abutted against the objective lens 34 fixed to the distal end of the lens tube 60 through the spacer tube 65, the lens 66, and the like. Therefore, the relay lens system 36 will not project from the lens tube 60 and move to the left.

The lens tube unit 59 is inserted in the inner tube 57. A ring 70, a notched compression ring 71 having a tapered outer circumferential surface, and a clamp ring 72 having a tapered inner circumferential surface are placed in the lens unit receptacle 61. Finally, a male screw 73a of a fixing ring 73 is screwed into a female screw 24c of the main body 24, thereby fixing the lens tube unit 59 in the axial direction. More specifically, when the fixing ring 73 pushes the clamp ring 72, the tapered portion of the inner circumferential surface of the clamp ring 72 acts on the tapered portion of the outer circumferential surface of the compression ring 71, thus decreasing the inner diameter of the compression ring 71. Then, the lens unit receptacle 61, the compression ring 71, and the clamp ring 72 become integral by the friction, and the compression ring 71 and the clamp ring 72 are sandwiched between the main body 24 and the fixing ring 73 through the ring 70 and fixed in the axial direction. Thus, the lens tube unit 59 is fixed to the main body 24 in the axial direction.

Of the components described above, those concerning indexing in the radial direction between the relay lens system 36 and the countersinks 31 serving as the pupil dividing stop are formed with a strict tolerance under an assumption that attachment and detachment are not performed. Thus, even if the relay lens system 36 and the countersinks 31 are rotated relative to each other (not for performing attachment and detachment), the radial offset becomes minimum. Also, in assembly of these components, they are adjusted so that they will not offset from each other in the radial direction as much as possible.

Because of this arrangement, the center of the optical axis of the relay lens system 36 and the centers of the rotation axes of the outer cylinder 26 to outer cylinder support portion 25 almost coincide with each other, and the amount of offset between the relay lens system 36 and countersinks 31 is very small when compared to that of a conventional case wherein attachment and detachment are performed.

As described above, the main body portion of the rigid stereoscopic endoscope 21 is an endoscope in which the outer cylinder 26 is stationary in the axial direction but is rotatable about the axis with respect to the inserting portion 22, the main body 24, and the outer cylinder support portion 25 that are coupled.

As shown in FIG. 2, the rigid stereoscopic endoscope 21 constitutes an integral optical lens body from the relay lens system 36 to the countersinks 31 of the pupil dividing means. As optical indexing is performed, the object image transmitted by the relay lens system 36 is divided into right and left object images having a sufficiently large parallax therebetween and a sufficiently high brightness by the countersinks 31 as the pupil dividing stop.

Since the optical axis of the relay lens system 36 and the centers of rotation axes of the outer cylinder 26 to the outer cylinder support portion 25 almost coincide with each other, a portion of the rigid stereoscopic endoscope 21 is rotatable between the outer cylinder 26 and the outer cylinder support portion 25. Even if the relay lens system 36 and the countersinks 31 are rotated relative to each other, the object image is divided into right and left object images having a sufficiently large parallax therebetween and a sufficiently high brightness by the countersinks 31.

To connect the rigid stereoscopic endoscope 21 and the camera head 37 to each other, the elongated projecting portion of the camera head mounting portion 30 of the rigid stereoscopic endoscope 21 shown in FIG. 2 is inserted and fitted in the elongated recessed portion 40 of the endoscope mounting portion 38 of the camera head 37 shown in FIG. 3, and the female screw 27a of the connecting ring 27 is screwed onto the male screw 41 of the endoscope mounting portion 38, thereby fixing the endoscope 21 and the camera head 37.

At this time, the flange portion 29 is abutted against the peripheral edge of the elongated recessed portion 40, thereby performing focusing at a portion between the rigid stereoscopic endoscope 21 and the camera head 37. A gap is present between the elongated projecting portion and the elongated recessed portion 40 in the radial direction, and the rigid stereoscopic endoscope 21 and the camera head 37 are sometimes coupled to each other with a slight offset. However, in the same manner as in the first embodiment, since the imaging lens 43 and CCDs 44 are formed in sizes enough to absorb this offset, the brightness of the right and left object images can be sufficiently obtained.

A light guide cable (not shown) coupled to a light source unit (not shown) is connected to the light guide cable mounting portion 33, thereby supplying illumination light to the object.

As described above, upon rotation of the rigid stereoscopic endoscope 21 between the outer cylinder 26 and the outer cylinder support portion 25, even if the relay lens system 36 and the countersinks 31 are rotated relative to each other, the light beams of the right and left object images are entirely received by the CCDs 44 without a loss, and the brightness of the right and left images is always sufficiently maintained.

To perform observation with this rigid stereoscopic endoscope 21, its inserting portion 22 is inserted in the target. At this time, the camera head 37 is supported such that the vertical direction of the CCDs 44 and the vertical direction of the operator coincide with each other (such that the partially cutout portion in FIG. 3 is directed upward).

To change the direction of the field of view, the support state of the camera head 37 is not changed, but the inserting portion 22 of the rigid stereoscopic endoscope 21 is rotated by the outer cylinder support portion 25. As the positional relationship between the CCDs 44 in the camera head 37 and the operator does not change, the display direction on the monitor of the CCDs 44 and the operating direction of the operator do not change. However, as the relay lens system 36 in the inserting portion 22 is rotated with respect to the CCDs 44 in the camera head 37, the direction of the field of view received by the CCDs 44 is changed. With this operation, only the direction of the field of view can be changed while maintaining the operating direction of the operator and the display direction on the monitor to coincide with each other.

To sterilize the rigid stereoscopic endoscope 21 after use, the camera head 37 is separated from the rigid stereoscopic endoscope 21 by removing the connecting ring 27, and the rigid stereoscopic endoscope 21 is cleaned and sterilized. When the inner side of the outer cylinder 26 is soiled through its countersinks 31, the inner side of the outer cylinder 26 is cleaned by an applicator or the like through the side holes 32. After cleaning, high-pressure steam sterilization is performed. After being sterilized in a high-pressure steam sterilizer, if the surface of the endoscope cover glass plate 46 of the outer cylinder 26 shown in FIG. 4 is fogged with the steam, the fogging is wiped from the side holes 32 in the same manner as in cleaning.

In this embodiment, since the pupil dividing means is rotatable with respect to the oblique-vision image transmitting means, only the direction of the field of view can be changed while maintaining the display direction on the monitor to coincide with the operating direction of the operator. Therefore, the operability is improved.

(Third Embodiment)

A rigid stereoscopic endoscope according to the third embodiment of the present invention will be described with reference to FIG. 5.

A rigid stereoscopic endoscope 75 of this embodiment is obtained by altering the oblique-vision endoscope of the second embodiment described above to a direct-vision endoscope. Other arrangements and components that are the same as those in the second embodiment are denoted by the same reference numerals as in the second embodiment, and a detailed description thereof will be omitted. In fine, the rigid stereoscopic endoscope 75 is constituted by a direct-vision inserting portion 76 and an operational holding portion 23.

How to connect a camera head 37 is the same as in the second embodiment described above, and the direction of the field of view does not change upon rotation of the direct-vision inserting portion 76 and the camera head 37 relative to each other. Thus, a light guide cable mounting portion 33 can be rotated to an arbitrary position without changing the direction of the field of view.

As the light guide cable mounting portion 33 can be rotated to an arbitrary position, a light guide cable to be mounted to it can be rotated to a position where it does not hinder the operability, thereby improving the operability.

(Fourth Embodiment)

Figure 6:
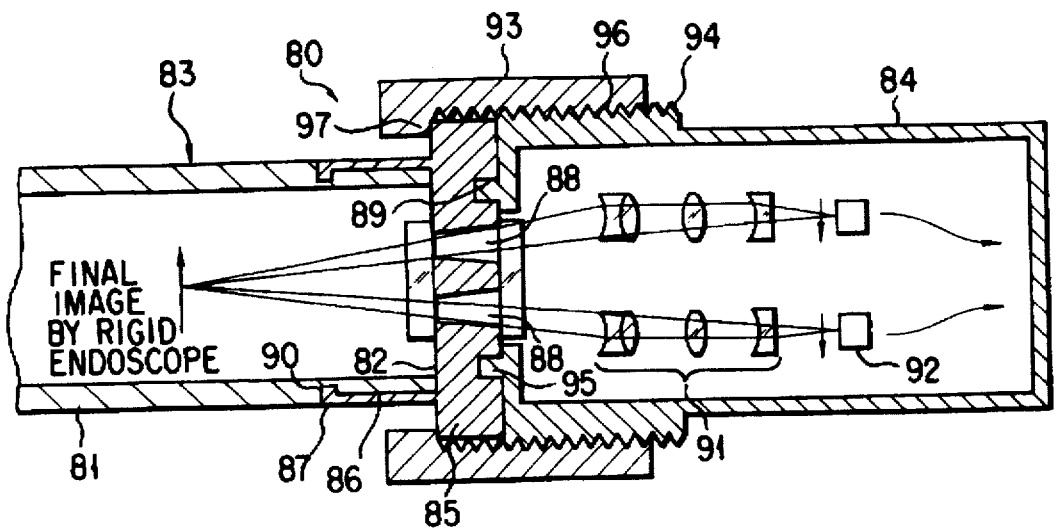
FIG. 6 is a diagram for schematically explaining a portion of a rigid stereoscopic endoscope according to the fourth embodiment of the present invention, showing the portion from an image transmitting optical system to an observation unit.

A rigid stereoscopic endoscope according to the fourth embodiment of the present invention will be described with reference to FIG. 6.

In the fourth to seventh embodiments to be described hereinafter, the image transmitting means and the pupil dividing means are detachable.

A rigid stereoscopic endoscope 80 of the fourth embodiment has the same arrangement as that of the second embodiment described above except that the arrangement of its pupil dividing stop is changed. As the operation obtained by the same arrangement is the same, the detailed description of the same arrangement and the same operation will thus be omitted.

The rigid stereoscopic endoscope 80 of this embodiment is constituted by a main body 83 having an oblique-vision observation type inserting portion (not shown), an operational holding portion 81, and a pupil dividing stop unit 82, and a camera head 84.

The pupil dividing stop unit 82 has a disk portion 85, a cylindrical thin portion 86 coaxially contiguously provided to the disk portion 85, and a holding portion coupling portion 87 formed on the distal end of the thin portion 86. The disk portion 85 has two pupil apertures 88 for dividing the light beam, and a plurality of positioning holes 89 for performing positioning with respect to the camera head 84. The thin portion 86 can be deformed easily in the radial direction. The distal end of the holding portion coupling portion 87 is engaged with a groove 90 formed in the outer surface of the operational holding portion 81. The thin portion 86 constitutes a snap fit portion which is rotatable about the operational holding portion 81 and removed upon application of a tensile force exceeding a predetermined value. Hence, the pupil dividing stop unit 82 is rotatable about and is detachable from the operational holding portion 81. Note that the pupil dividing stop unit 82 is formed with a selected combination of components so that the center of the optical axis of the relay lens system and the center of rotation axis of the snap fit portion coincide with each other, thereby ensuring indexing of the relay lens system (not shown) and the pupil apertures 88. The optical system constituted by the relay lens system and the pupil dividing means is integrally incorporated in the main body 83. An integral optical lens body in which the relay lens system and the pupil dividing means are incorporated is constituted.

The operational holding portion 81 and the pupil dividing stop unit 82 are detachable from each other and integrally assembled to each other in a one-to-one correspondence so that the gap of the snap fit portion in the radial direction becomes minimum. The pupil dividing stop unit 82 and the camera head 84 need not form an integral pair in a one-to-one correspondence but can be replaced, as in the embodiments described above.

Imaging lenses 91 serving as the stereoscopic imaging means, and CCDs 92 are provided in the camera head 84. A connecting ring coupling portion 94 and positioning pins 95 are provided to the outer side of the camera head 84. The connecting ring coupling portion 94 comprises a male screw for mounting a connecting ring 93 (described later) thereon. The positioning pins 95 are coupled to the positioning holes 89 to perform positioning with respect to the main body 83 side. A gap is present between the positioning pins 95 and the positioning holes 89 in the radial direction. Since the imaging lenses 91 and the CCDs 92 are formed to a comparatively large size in the same manner as in the first and second embodiments described above, the brightness of the right and left object images is sufficiently obtained. The connecting ring 93 consists of a camera head connecting portion 96 comprising a female screw, and a small-diameter retaining portion 97 for preventing removal of the main body 83 in the radial direction.

To connect the camera head 84 to the main body 83, the positioning pins 95 of the camera head 84 are fitted in the positioning holes 89 of the pupil dividing stop unit 82 of the main body 83, the connecting ring 93 is set from the main body 83, and the female screw of the connecting ring 93 is screwed onto the male screw of the camera head 84. Thus, the retaining portion 97 pushes the disk portion 85 of the pupil dividing stop unit 82 of the main body 83 toward the camera head 84, so that the pupil dividing stop unit 82 is fixed to the camera head 84 without an axial backlash. Although the pupil dividing stop unit 82 is mounted with an offset in the radial direction by a distance corresponding to the gap between the positioning pins 95 and the positioning holes 89, since the imaging lenses 91 and the CCDs 92 are formed to a comparatively large size in the same manner as in the second embodiment, the brightness of the right and left object images is not decreased.

To change the direction of the field of view, the camera head 84 is fixed to the operator, and the operational holding portion 23 is rotated, so that only the direction of the field of view can be changed while maintaining the display direction on the monitor to coincide with the operating direction of the operator.

When a rotating portion between the operational holding portion 81 and the pupil dividing stop unit 82 or the inner side of the pupil apertures 88 is soiled, the main body 83 and the camera head 84 are separated from each other by removing the connecting ring 93, and the operational holding portion 81 and the pupil dividing stop unit 82 are separated from each other by pulling the pupil dividing stop unit 82 from the operational holding portion 81 in the axial direction. Then, the entire surfaces can be exposed to the outside and cleaned. The camera head 84 and the pupil dividing stop unit 82 may be separated from each other by separating the operational holding portion 81 and the pupil dividing stop unit 82 first and thereafter removing the connecting ring 93.

Regarding the attaching/detaching portion, the radial offset of which influences the brightness of the images, its offset is suppressed by combining correspondence within such a range that they are detachable from each other. Hence, the radial offset does not influence the brightness of the images. As the compatibility of this attaching/detaching portion is maintained by setting a predetermined gap in it, the offset can be decreased compared to that of the conventional case, although it is inferior to that of the second embodiment. Since the pupil dividing stop unit 82 portion can be removed, the components constituting the pupil dividing stop unit 82 can be cleaned well.

(Fifth Embodiment)

Figure 7:
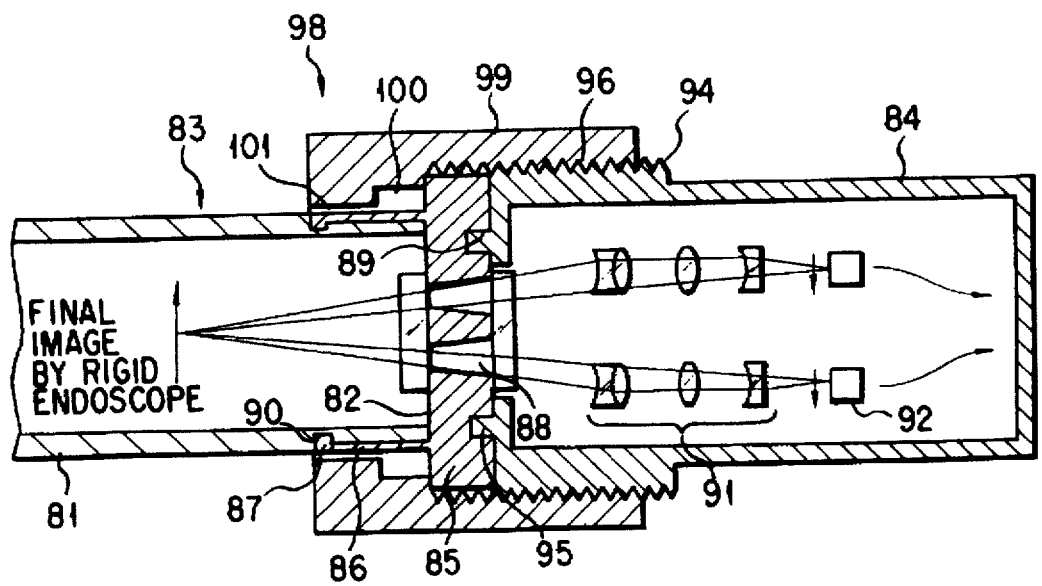
FIG. 7 is a diagram for schematically explaining a portion of a rigid stereoscopic endoscope according to the fifth embodiment of the present invention, showing the portion from an image transmitting optical system to an observation unit.

A rigid stereoscopic endoscope according to the fifth embodiment of the present invention will be described with reference to FIG. 7.

A rigid stereoscopic endoscope 98 of this embodiment is different from that of the fourth embodiment in that the arrangement of its connecting ring is changed. Other arrangements and components that are the same as those in the fourth embodiment are denoted by the same reference numerals as in the fourth embodiment, and a detailed description thereof will be omitted.

A connecting ring 99 of the fifth embodiment is provided with a camera head connecting portion 96 comprising a female screw, a small-diameter first retaining portion 100, and a second retaining portion 101 having a smaller diameter than that of the first retaining portion 101. The retaining portion 100 prevents removal of a main body 83 in the axial direction. The retaining portion 101 suppresses elastic deformation of a pupil dividing stop 82 in the radial direction.

The main body 83 and a camera head 84 are connected to each other almost in the same manner as in the fourth embodiment described above. Note that in place of the retaining portion 97, the first retaining portion 100 pushes a disk portion 85 toward the camera head 84.

When a rotating portion between an operational holding portion 81 and the pupil dividing stop 82 or the interior of apertures 88 is soiled, the main body 83 and the camera head 84 are separated from each other by removing the connecting ring 99, and the operational holding portion 81 and the pupil dividing stop 82 are separated from each other by pulling the pupil dividing stop 82 from the operational holding portion 81 in the axial direction. Then, the entire surfaces of the components can be exposed to the outside and can be cleaned.

Before removing the connecting ring 99, even if the operational holding portion 81 and the pupil dividing stop 82 are pulled in the opposite directions to separate them, they will not be separated from each other unless the connecting ring 99 is removed, as the retaining portion 101 suppresses the thin portion 86 from being elastically deformed in the radial direction.

With the arrangement of this embodiment, in addition to the effect of the fourth embodiment described above, even if the operational holding portion 81 and the camera head 84 are pulled in the opposite directions during connection of the connecting ring 99, they will not be separated from each other. Thus, separation of the main body 83 and the camera head 84 by an erroneous operation can be prevented.

(Sixth Embodiment)

Figure 8:
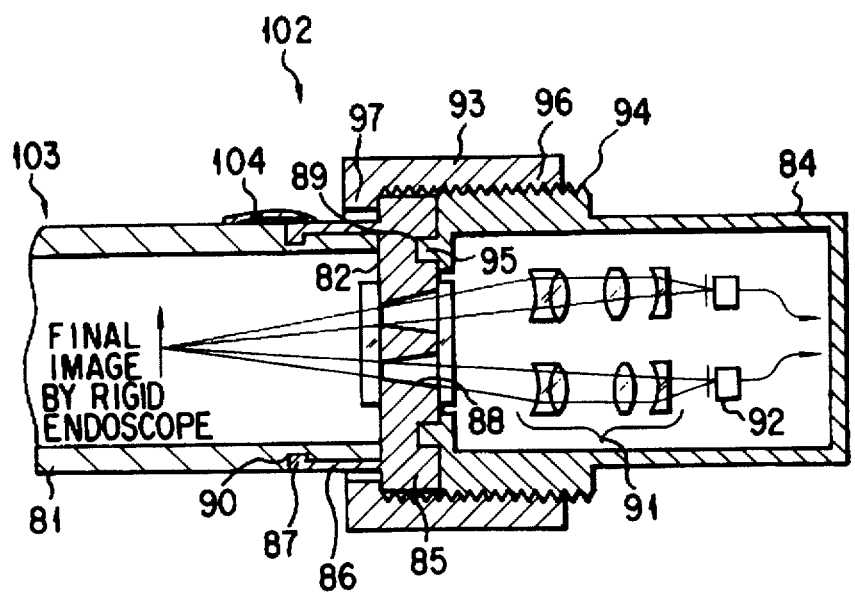
FIG. 8 is a diagram for schematically explaining a portion of a rigid stereoscopic endoscope according to the sixth embodiment of the present invention, showing the portion from an image transmitting optical system to an observation unit.

A rigid stereoscopic endoscope according to the sixth embodiment of the present invention will be described with reference to FIG. 8.

A rigid stereoscopic endoscope 102 of the sixth embodiment is different from that of the fourth embodiment in that the connecting arrangement of its operational holding portion 81 and pupil dividing stop 82 is changed. Other arrangements and components that are the same as those in the fourth embodiment are denoted by the same reference numerals as in the fourth embodiment, and a detailed description thereof will be omitted.

A main body 103 of the rigid stereoscopic endoscope 102 is constituted by the operational holding portion 81, the pupil dividing stop 82, a coupling member 104 for coupling the operational holding portion 81 and the pupil dividing stop 82, and an oblique-vision inserting portion (not shown). The coupling member 104 comprises, e.g., a small-diameter chain, and has sufficiently large length and strength. The coupling member 104 also has a thinness not interfering with a retaining portion 97 when passing a connecting ring 93. The two ends of the coupling member 104 are fixed to the operational holding portion 81 and the pupil dividing stop 82. Thus, even when the operational holding portion 81 and the pupil dividing stop 82 are separated from each other, they are connected to each other through the coupling member 104.

The operation of the rigid stereoscopic endoscope 102 and connection between the main body 103 and a camera head 84 are almost the same as those in the fourth embodiment. As the coupling member 104 has a small diameter, it will not interfere with the operation by the operator. When a rotating portion between the operational holding portion 81 and the pupil dividing stop 82 or the interior of apertures 88 is soiled, the main body 103 and the camera head 84 are separated from each other by removing the connecting ring 93, and the snap fit of the pupil dividing stop operational holding portion 81 and the pupil dividing stop 82 is separated by pulling the pupil dividing stop 82 from the operational holding portion 81 in the axial direction. Then, all the surfaces of the components can be exposed to the outside and can be cleaned. Even after the snap fit is separated, the portion from the operational holding portion 81 to the pupil dividing stop 82 is coupled through the coupling member 104.

With this arrangement, in addition to the effect of the fourth embodiment, when separating the snap fit, since the portion from the operational holding portion 81 to the pupil dividing stop 82 is coupled with the coupling member 104, the pupil dividing stop 82 will not be lost.

(Seventh Embodiment)

Figure 9:
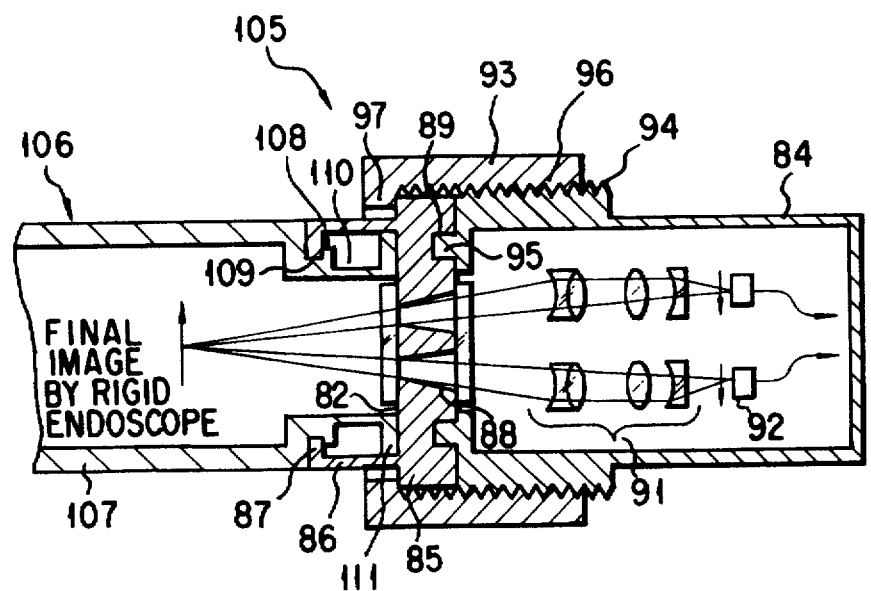
FIG. 9 is a diagram for schematically explaining a portion of a rigid stereoscopic endoscope according to the seventh embodiment of the present invention, showing the portion from an image transmitting optical system to an observation unit.

A rigid stereoscopic endoscope according to the seventh embodiment of the present invention will be described with reference to FIG. 9.

A rigid stereoscopic endoscope 105 of the seventh embodiment is obtained by changing the arrangement of the groove portion of the snap fit portion of the fourth embodiment described above. Other arrangements and components that are the same as those in the fourth embodiment are denoted by the same reference numerals as in the fourth embodiment, and a detailed description thereof will be omitted.

A main body 106 is constituted by an operational holding portion 107, a pupil dividing stop 82, and an oblique-vision inserting portion (not shown). A distal end-side first groove 109 and a proximal end-side second groove 110 are provided adjacent to each other on the outer surface of the operational holding portion 107 with a projection 108 therebetween. A holding portion coupling portion 87 supported by a thin portion 86 that can be elastically deformed easily is located in either the first or second groove 109 or 110. In the first groove 109, the holding portion coupling portion 87 is rotatable but is stationary in the axial direction. In the second groove 110, the holding portion coupling portion 87 is engaged with it so as to be rotatable and movable in the axial direction.

Movement of the holding portion coupling portion 87 from the first groove 109 to the second groove 110 is achieved by elastically deforming the thin portion 86 by pulling or pushing the operational holding portion 107 and the pupil dividing stop 82 in the axial direction, so that the holding portion coupling portion 87 rides over the projection 108. The amount of elastic deformation of the thin portion 86 is set such that the holding portion coupling portion 87 will not ride over a removal stopper 111.

In observation, the holding portion coupling portion 87 is located in the first groove 109. To change the field of view, the holding portion coupling portion 87 is rotated in the first groove 109.

When a rotating portion between the operational holding portion 107 and the pupil dividing stop unit 82 or the interior of apertures 88 is soiled, the main body 106 and a camera head 84 are separated from each other by removing a connecting ring 93, the holding portion coupling portion 87 is located in the second groove 110 by pulling the pupil dividing stop 82 from the operational holding portion 107 in the axial direction, and the distance between the operational holding portion 107 and the pupil dividing stop 82 is increased. Then, the portion between the operational holding portion 107 and the pupil dividing stop 82 can be cleaned easily.

(Eighth Embodiment)

A rigid stereoscopic endoscope according to the eighth embodiment of the present invention will be described with reference to FIGS. 10 to 12.

A rigid stereoscopic endoscope 120 of the eighth embodiment is different from that of the second embodiment described above in that the arrangement of its pupil dividing stop is changed. Other arrangements and components that are the same as those in the fourth embodiment are denoted by the same reference numerals as in the fourth embodiment, and a detailed description thereof will be omitted.

The rigid stereoscopic endoscope 120 of this embodiment has an integral body consisting of an oblique-vision inserting portion (not shown), an operational holding portion 121, and a pupil dividing stop 122, i.e., a main body 123 in which at least an integral optical lens system is to be incorporated, and a camera head 124 coupled to the main body 123.

Figure 11:
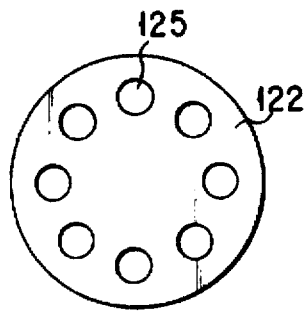
FIG. 11 is a front view of a pupil dividing stop member of the eighth embodiment.

As shown in FIG. 11, in the pupil dividing stop 122, eight pupil apertures 125 for dividing the light beam are point symmetrically arranged at an angular interval of 45° about the center of the optical axis of the relay lens system. A plurality of positioning holes 126 for positioning the camera head 124 are formed in the operational holding portion 121. The camera head 124 is constituted by a rotating portion 127, a rotation support portion 128, and a camera head body 129. The rotating portion 127 is provided with a flange portion 130. The flange portion 130 is sandwiched between the rotation support portion 128 coupled to the camera head body 129 with a screw or the like (not shown), and the camera head body 129, so that the rotating portion 127 is stationary in the axial direction but is rotatable about its axis. The rotating portion 127 is provided with positioning pins 131 for performing positioning with respect to the optical lens system body 123 of the rigid stereoscopic endoscope 120.

The rotating portion 127 is provided with a connecting ring mounting portion 132 comprising a male screw which is to be connected to a connecting ring 139 (to be described later).

A gap is defined in the positioning pins 131 and the positioning holes 126 in the radial direction. This is the same as in the second embodiment described above.

Figure 10:
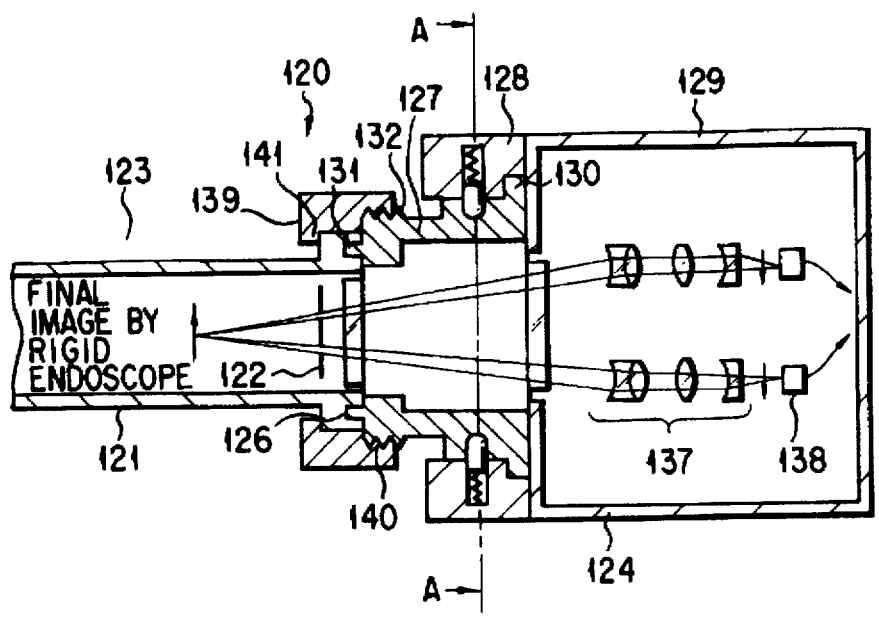
FIG. 10 is a diagram for schematically explaining a portion of a rigid stereoscopic endoscope according to the eighth embodiment of the present invention, showing the portion from an image transmitting optical system to an observation unit.
Figure 12:
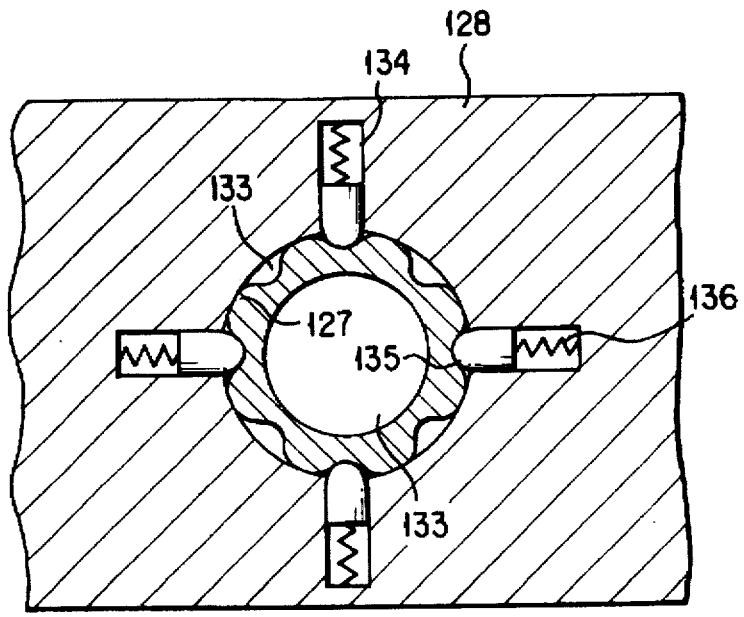
FIG. 12 is a sectional view taken along the line A—A of FIG. 10.
Figure 13:
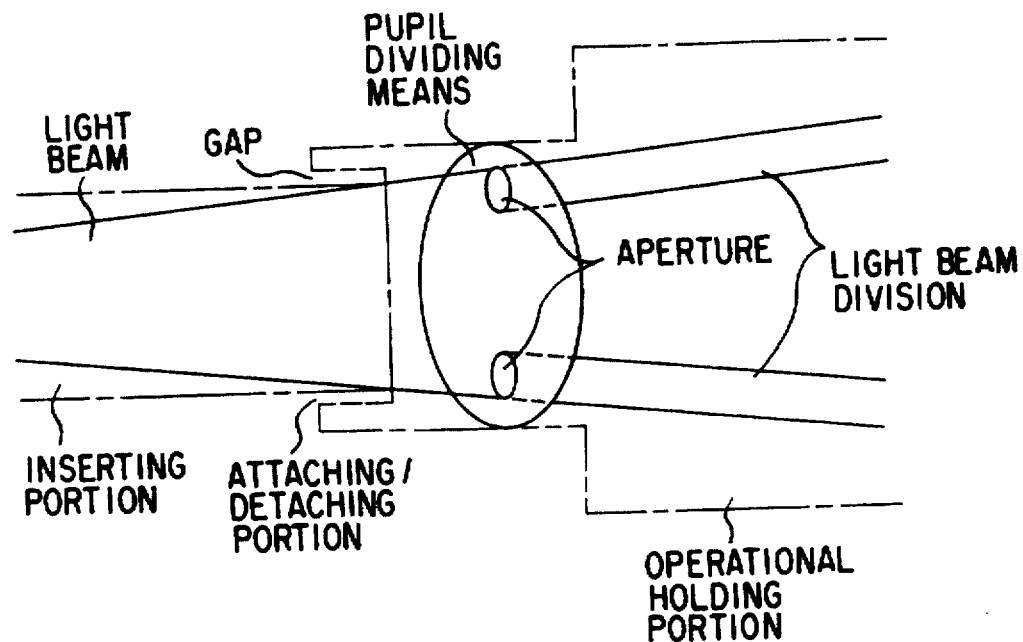
FIG. 13 is a diagram for explaining a conventional pupil dividing unit.
Figure 14:
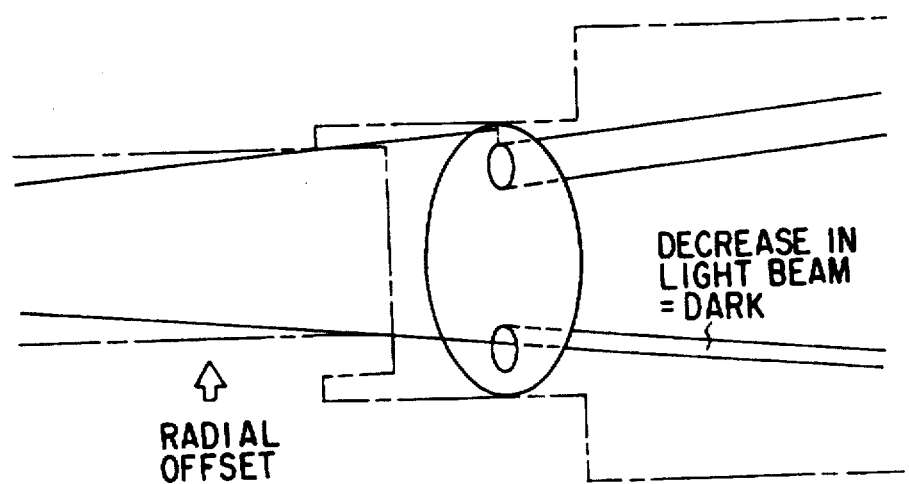
FIG. 14 is a diagram for explaining the poorly functioning state of the conventional pupil dividing unit.

FIG. 12 is a sectional view taken along the line A—A of FIG. 10. As shown in FIG. 12, grooves 133 are formed in the outer surface of the rotating portion 127 at an angular interval of 45°. Holes 134 are formed in the rotation support portion 128 at an angular interval of 90° to oppose the corresponding grooves 133. A pin 135 and a spring 136 are incorporated in each hole 134. The pins 135 are biased by the corresponding springs 136 toward the peripheral portion of the rotating portion 127.

Imaging lenses 137 and CCDs 138 are provided in the camera head body 129. The imaging lenses 137 and the CCDs 138 are formed to a comparatively large size with respect to the object images. This is the same as in the second embodiment described above.

The rotation support portion 128 is fixed to the camera head body 129 at a position with which the center of the optical axis of the imaging lens 137 and CCDs 138 and the center of the optical axis of the apertures 125 coincide with each other for each of the right and let images when the optical lens system body 123 and the camera head 124 are coupled to each other.

A connecting ring 139 consists of a camera head connecting portion 140 comprising a female screw, and a small-diameter retaining portion 141 for preventing removal of the operational holding portion 121 in the axial direction.

To connect the optical lens system body 123 of the rigid stereoscopic endoscope 120 to the camera head 124, the positioning holes 126 of the connecting ring 139 are fitted with the positioning pins 131 of the rotating portion 127, the connecting ring 139 is applied from the operational holding portion 121 side, and the female screw of the connecting ring 139 is screwed onto the male screw of the rotating portion 127. Then, when the retaining portion 141 pushes the operational holding portion 121 toward the rotating portion 127, the operational holding portion 121 is fixed to the rotating portion 127 without an axial backlash. The operational holding portion 121 is mounted to the rotating portion 127 with a radial offset by a distance corresponding to the radial gap between the positioning pins 131 and the positioning holes 126. However, the brightness of the images is not decreased, in the same manner as in the second embodiment.

To change the direction of the field of view, the camera head 124 is fixedly held by the operator, and the operational holding portion 121 side is rotated. As shown in FIG. 12, the grooves 133 are formed in the rotating portion 127, and the pins 135 in the rotation support portion 128 are held as they are pushed by the springs 136 toward the grooves 133. When the rotating portion 127 coupled to the operational holding portion 121 is rotated with a force equal to or larger than the pressure of the springs 136, the grooves 133 push the pins 135 to compress the springs 136, so that the pins 135 are pushed out from the grooves 133 and the rotating portion 127 is rotated. Since the grooves 133 of the rotating portion 127 are formed at an angular interval of 45°, the rotating portion 127 is rotated at an angular pitch of 45°.

The pupil dividing stop 122 in the operational holding portion 121 fixed to the rotating portion 127 is indexed with respect to the relay lens system, as described regarding the arrangement of the rigid stereoscopic endoscope 120. Thus, the brightness of images obtained by dividing the light beam into eight portions (every 45°) is maintained.

Since the rotating portion 127 is rotated at an angular pitch of 45°, as described above, of the divided images, two images are always guided to the imaging lenses 137 and the CCDs 138. In this manner, only the direction of the field of view can be changed, although at an angular pitch of 45°, while maintaining the display direction on the monitor to coincide with the operating direction of the operator.

In this embodiment, the grooves are formed at an angular interval of 45°. However, the angular interval of the grooves is not limited to this, but can be larger or smaller than this. The same applies to the angular interval (90°) of the holes.

According to this embodiment, since the image transmitting means and the pupil dividing means are fixed, radial adjustment of the pupil dividing means can be correctly and easily performed manually with the image transmitting means. In addition, only the direction of the field of view can be changed, although it is limited to an angular pitch of 45°, while maintaining the display direction on the monitor to coincide with the operating direction of the operator, thereby improving the operability.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A pupil division type stereoscopic endoscope comprising:

an image transmitting optical system having an image-forming lens for forming an image of an object and a relay lens for transmitting the image formed by said image-forming lens, said image transmitting optical system having an optical axis;

a pupil dividing unit for dividing the image transmitted by said image transmitting optical system into a plurality of object images having a parallax therebetween;

an observation unit for receiving the plurality of object images obtained through division by said pupil dividing unit, and for displaying the plurality of object images so as to enable stereoscopic observation;

an optical lens system main body which integrally incorporates said image transmitting optical system and said pupil dividing unit so that said image transmitting optical system and said pupil dividing unit are coupled to and not detachable from each other;

a connecting unit for detachably coupling said optical lens system main body and said observation unit to each other; and a position adjusting device for adjusting optical positions of said image transmitting optical system and said pupil dividing unit relative to each other in a direction of the optical axis of said image transmitting optical system.

2. An endoscope according to claim 1, wherein said observation unit includes imaging means for imaging the plurality of object images.

3. An endoscope according to claim 1, wherein said image transmitting optical system and said pupil dividing unit are rotatable relative to each other about the optical axis of said image transmitting optical system as a center.

4. An endoscope according to claim 1, wherein said pupil dividing unit includes a pupil dividing stop.

5. An endoscope according to claim 1, wherein said optical lens system main body includes a hermetic structure which does not allow communication of a gas between inner and outer portions thereof, and wherein said image transmitting optical system is provided in said optical lens system main body within said hermetic structure and said pupil dividing unit is provided in said optical lens system main body outside said hermetic structure.

6. An endoscope according to claim 1, wherein said image transmitting optical system includes a lens group.

7. An endoscope according to claim 1, wherein said pupil dividing unit is assembled in said optical lens system main body to be rotatable with respect to said image transmitting optical system about the optical axis of said image transmitting optical system.

8. A pupil dividing stereoscopic endoscope comprising:

image transmitting means for forming an image of an object and for transmitting the formed image;

pupil dividing means for dividing the image transmitted by said image transmitting means into a plurality of object images having a parallax therebetween;

observing means for receiving the plurality of object images obtained through division by said pupil dividing means, and for displaying the plurality of object images so as to enable stereoscopic observation;

an optical lens system main body which integrally incorporates said image transmitting means and said pupil dividing means so that said image transmitting means and said pupil dividing means are coupled to and not detachable from each other;

connecting means for detachably coupling said optical lens system main body and said observing means to each other; and a position adjusting means for adjusting optical position of said image transmitting means and said pupil dividing means relative to each other in a direction of the optical axis of said image transmitting means.

* * * * *